(12) United States Patent
Buncke (10) Patent No.: US 6,245,091 B1
(45) Date of Patent: Jun. 12, 2001

(54) VIBRATING SUCTION SURGICAL NEEDLE

(75) Inventor: Harry J. Buncke, Hillsborough, CA (US)

(73) Assignee: Frank Hoffman, Hillsborough, CA (US); a part interest (*) Notice: Subject to any disclaimer, the term of this patent is extended or adjusted under 35 U.S.C. 154(b) by 0 days.

(21) Appl. No.: 09/252,735

(22) Filed: Feb. 19, 1999

(51) Int. Cl.$^7$ .................................................. A61B 17/06
(52) U.S. Cl. ............................................................. 606/222
(58) Field of Search .................................. 606/185, 186, 606/169, 9, 15, 13; 81/9.22; 604/22

(56) References Cited

U.S. PATENT DOCUMENTS

| | | |
|---|---|---|
| 3,896,811 * | 7/1975 | Storz ................................... 128/24 A |
| 3,990,452 * | 11/1976 | Murry et al. ........................ 128/24 A |
| 4,103,689 | 8/1978 | Leighton . |
| 4,180,079 * | 12/1979 | Wing ...................................... 607/69 |
| 4,356,823 | 11/1982 | Jackson . |
| 4,493,694 | 1/1985 | Wuchinich . |
| 4,708,717 | 11/1987 | Deane . |
| 4,730,635 | 3/1988 | Linden . |
| 4,886,491 | 12/1989 | Parisi . |
| 5,199,943 | 4/1993 | Wypych . |
| 5,254,082 | 10/1993 | Takase . |
| 5,380,273 | 1/1995 | Dubrul . |
| 5,484,398 | 1/1996 | Stoddard . |
| 5,514,086 | 5/1996 | Parisi . |
| 5,549,119 | 8/1996 | Solar . |
| 5,562,609 | 10/1996 | Brumbach . |
| 5,562,610 * | 10/1996 | Brumbach ............................... 604/22 |
| 5,645,537 | 7/1997 | Powles . |
| 5,902,279 * | 5/1999 | Powles et al. ........................ 604/239 |
| 5,984,915 * | 11/1999 | Loeb et al. ............................. 606/15 |
| 5,997,531 * | 12/1999 | Loeb et al. ............................. 606/15 |

* cited by examiner

Primary Examiner—Henry J. Recia
Assistant Examiner—Tan-Uyen T. Ho
(74) Attorney, Agent, or Firm—Thomas M. Freiburger

(57) ABSTRACT

A surgical needle is attached to a handle which includes a vibrating device for inducing vibrations in a prescribed frequency range to the needle. The needle's vibration helps avoid damage to major blood vessels and nerves when the needle is pushed through subcutaneous patient tissue. In one form the needle has provision to grip the end of a suture, so that the suture may be attached after the needle is pushed through and emerges out of subcutaneous tissue. In a face-lift operation the needle may be pushed through a path where support is desired, then the end of a one-way suture can be attached to the distal end of the needle, after which the one-way suture can be retracted so that the one-way suture occupies the same path where the needle was inserted. The suture attachment can be via a hollow bore through the needle, with suction applied through the handle, so that the end of the suture can be drawn into the needle from the needle's distal end, retaining the suture to the needle when the needle is retracted from the tissue. After such insertion of a one-way suture, the suture can be tensioned from the distal end so as to pull and maintain the desired tension in the skin tissue.

11 Claims, 8 Drawing Sheets

VIBRATING SUCTION SURGICAL NEEDLE

BACKGROUND OF THE INVENTION

This invention concerns surgical needles and procedures for their use. In particular the invention relates to a needle which can be vibrated to aid in passing through tissue and which, in some embodiments, has provision for attaching to a suture to pull the suture through tissue as the needle is retracted.

Application Ser. No. 859,887, now U.S. Pat. No. 5,931,855, discloses a one-way surgical suture and methods for its use. The sutures have barbs enabling passage through tissue in one direction, but not the other, so that wounds can be closed by a pair of such one-way sutures oriented oppositely on opposed sides of a wound and connected together, or, as the pending application discloses, by a double armed suture with barbs in opposite directions, both ends implanted into opposite sides of the wound. The copending application discloses several methods for use of such one-way sutures. This invention is concerned with a surgical needle apparatus particularly useful with such one-way sutures, and also with a cooperating feature which helps avoid blood vessels and nerves as the needle is pushed through the patient's tissue.

The following patents have some relevance to the subject matter of this invention: U.S. Pat. Nos. 4,103,689, 4,356,823, 4,493,694, 4,708,717, 4,730,635, 4,886,491, 5,199,943, 5,254,082, 5,380,273, 5,514,086, 5,484,398, 5,549,119, 5,562,609, 5,562,610, 5,645,537. Most of these patents are concerned with medical devices involving suction, or ultrasonic vibration, or both. The suction is generally applied to the medical instrument for the purpose of drawing fragments of tissue out of the body, often after portions of tissue have been shattered using ultrasonic energy transmitted from the tip of the tool.

Of the above patents, U.S. Pat. No. 5,549,119 describes a vibrating tip catheter or guidewire which is vibrated for the purpose of passing through tortuous anatomical pathways, the vibration being intended to enhance the ability of the catheter or guidewire to pass through the narrow pathways or to cross lesions or stenoses. In that patent the vibrations can be achieved with a microvibrating motor integral with the catheter or guidewire, the frequency and amplitude of vibration being adjustable via an external control device. The instrument seems primarily concerned with movement through a blood vessel, particularly for angioplasty and atharectomy.

Medical devices of the prior art have not been effective for the purposes of the present invention, and have not included a surgical suturing needle which vibrates at a sub-ultrasonic frequency to aid in passing the needle through tissue, or a surgical needle which is hollow, with means for gripping the end of a suture.

SUMMARY OF THE INVENTION

In a principal embodiment of the present invention, a surgical needle is attached at its base end to a hollow handle having provision for vibrating the needle. This vibration could be via an internal electric motor, but in a preferred form the vibration is induced by a suction-operated device served by a suction line connected to the handle. When the surgical needle, vibrating at a frequency well below ultrasonic (usually in very low audible range, e.g. a range of about 20 to 30 per second) is pushed through subcutaneous patient tissue, the vibratory force permits the needle to be passed smoothly through the tissue, avoiding damage to major blood vessels and nerves. In tendon surgery, the needle tends to slide down the core of the tendon as it follows the longitudinal fibers of the tendon.

One type of suction-operated vibration inducer which can be included in the handle is a wheel with vanes, caused to rotate by the passage of air via the suction. The wheel has eccentric weighting, so as to cause vibration, and the handle is vented appropriately to allow the suction passage of air at sufficient velocity through the vaned wheel. Another type of vibratory device can be a flutter valve, such as a rubber duckbill valve which vibrates as air pulses through.

Once the needle, which may be a lengthy needle in the case of a face-lift operation, has been passed through the desired path and its sharp end exposed, the needle has provision for attaching to a suture, to enable the surgeon to pull the suture through the same path that has been occupied by the needle. The suture attachment device could be at either end of the needle, but in a specific embodiment it is at the distal, sharp end of the needle so that the surgeon can attach a one-way suture with barbs along its length and retract the needle by its handle, pulling the one-way suture in a reverse direction along the same path where the needle was inserted.

One arrangement for retaining the suture end to the needle includes the use of a hollow needle, with suction applied to the needle from the proximal end, thus enabling the needle to draw the suture end firmly into the needle to hold the suture for pulling it back through the tissue. This procedure is particularly useful in face-lifts, where a one-way suture is drawn back through the tissue in the permitted direction, then tension can later be applied to the distal end of the suture to pull and maintain tension in the skin tissue.

In one embodiment of the invention the tubular needle has an angled distal end, only the tip portion of which is sharpened. This, in conjunction with the vibration, helps avoid damage to vessels and nerves. The needle preferably is capable of disconnection from the handle and replaceable with a new needle.

The invention also encompasses methods for use of the vibrating needle, with or without the suction feature for retaining suture ends to the needle. These methods include the implantation and use of double-armed sutures having barbs extending in opposite directions on opposed sides of a midpoint of the suture. By one procedure, the needle of the invention is inserted through a lengthy path of subcutaneous tissue, from which it emerges at its distal end, an end of a double-armed suture is drawn into the hollow needle by suction from the handle, and the needle is retracted out from the tissue, drawing the one-way suture into the same path, in the direction permitted by the barbs. Then the procedure is repeated from the opposite direction to the same distal emerging point, where the other end of the suture, with the oppositely-directed barbs, is pulled through tissue in the opposite direction until the suture is fully implanted. Tension can then be applied to the tissue by drawing the double-armed suture tight.

It is among the objects of the invention to improve on surgical techniques, including face-lifts and plastic surgery, by use of a surgical needle useful in avoiding damage when passed through subcutaneous tissue and useful particularly for implanting one-way sutures. These and other objects, advantages and features of the invention will be apparent from the following description of preferred embodiments, considered along with the accompanying drawings.

DESCRIPTION OF PREFERRED EMBODIMENTS

Figures 1, 2:
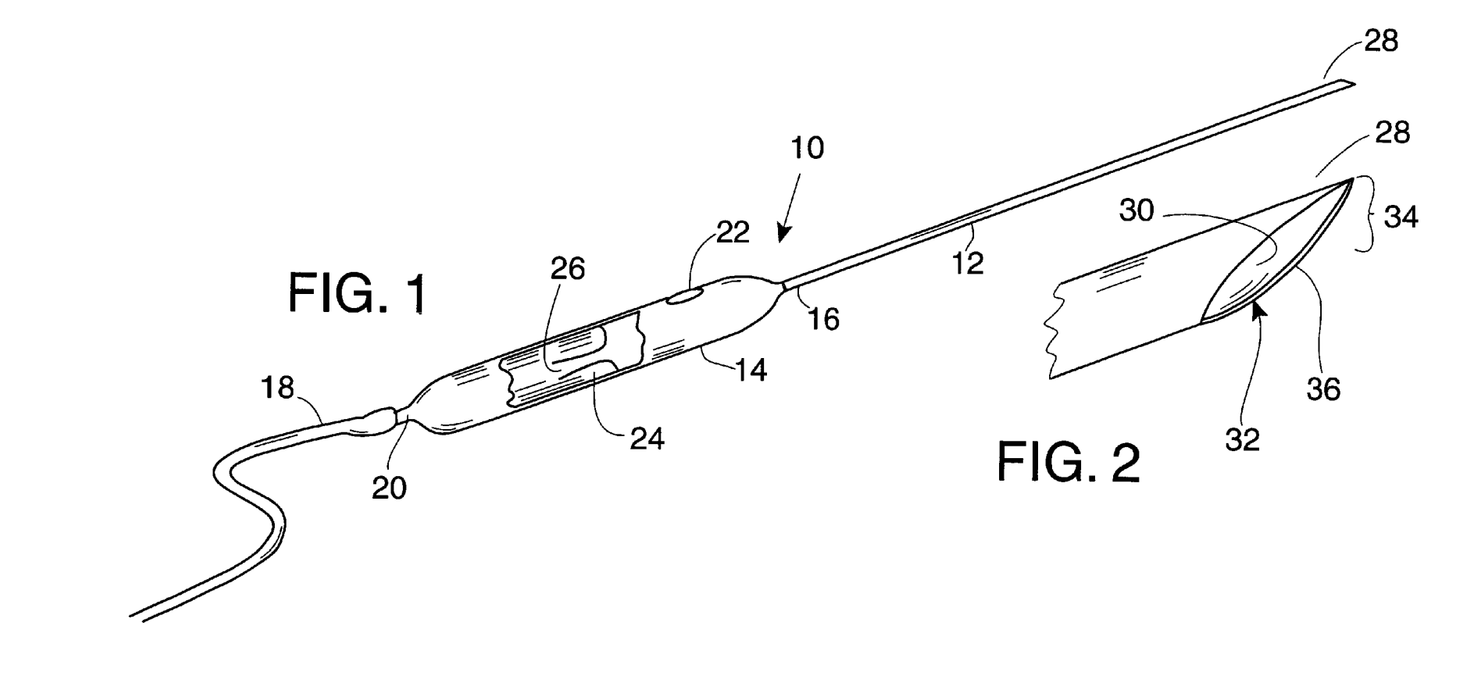
FIG. 1 is a side view partially cut away showing one form of a surgical needle according to the invention, having a handle with suction-induced vibration.
FIG. 2 is a side view showing a tip end of a hollow needle which preferably forms a part of the invention.

FIG. 1 shows a surgical needle apparatus 10, which includes a suturing needle 12 and a handle or housing 14 secured to the proximal end 16 of the needle. As noted above, the handle preferably has provision (not shown) for removal and replacement of the needle 12. The figure also illustrates a suction line 18 connected to a rear connection port 20 of the handle, and a vent opening 22 which allows air to pass through the handle, drawn by the suction in the suction line 18.

The handle 14 can be similar in size and shape to a known aspirator device sometimes referred to by physicians as a "tonsil sucker".

The vent 22, which may be manually switchable between open and closed, activates a vibration inducing device 24 within the handle, so as to provide vibration of a desired frequency and amplitude in the handle, that vibration being transferred to the needle 12. The vibration is far below ultrasonic, and may be in the frequency range of about 20 to 30 hertz, although any frequency that will cause vibrations effective for the purpose of the invention can be used. The form of vibratory device 24 shown in FIG. 1 is a flutter valve, normally closed by the relaxed state of the rubbery material from which it is made, but causing a fluttering vibration when air rushes through toward the suction line 18. The valve 24 may be configured as a duckbill valve, with a normally closed slit 26 which opens under sufficient force of air, then flutters open and closed repeatedly as air passes through, somewhat like the function of a duck call or reed instrument. The frequency and amplitude of vibration will be proportional to negative pressure of suction.

The needle 12 shown in FIG. 1 is a hollow needle, in one specific embodiment of the invention. Such a hollow needle may be approximately the size of an 18 gauge hypodermic needle. FIG. 2 shows a distal end or tip 28 of the needle, revealing a hollow, open interior 30. It is preferable that the distal end 28 of the hollow needle be angled or beveled as shown, and the beveled edge 32 in one preferred form of the invention is sharpened only in the distal region 34 of the tip. The sharpened portion 34 helps the needle pass through tissue, but the remaining portion 36 of the angled end, being rounded and not sharp, helps avoid damage as the vibrating needle pushes its way around blood vessels, nerves and other internal features where damage should be avoided.

Figures 3, 3A:
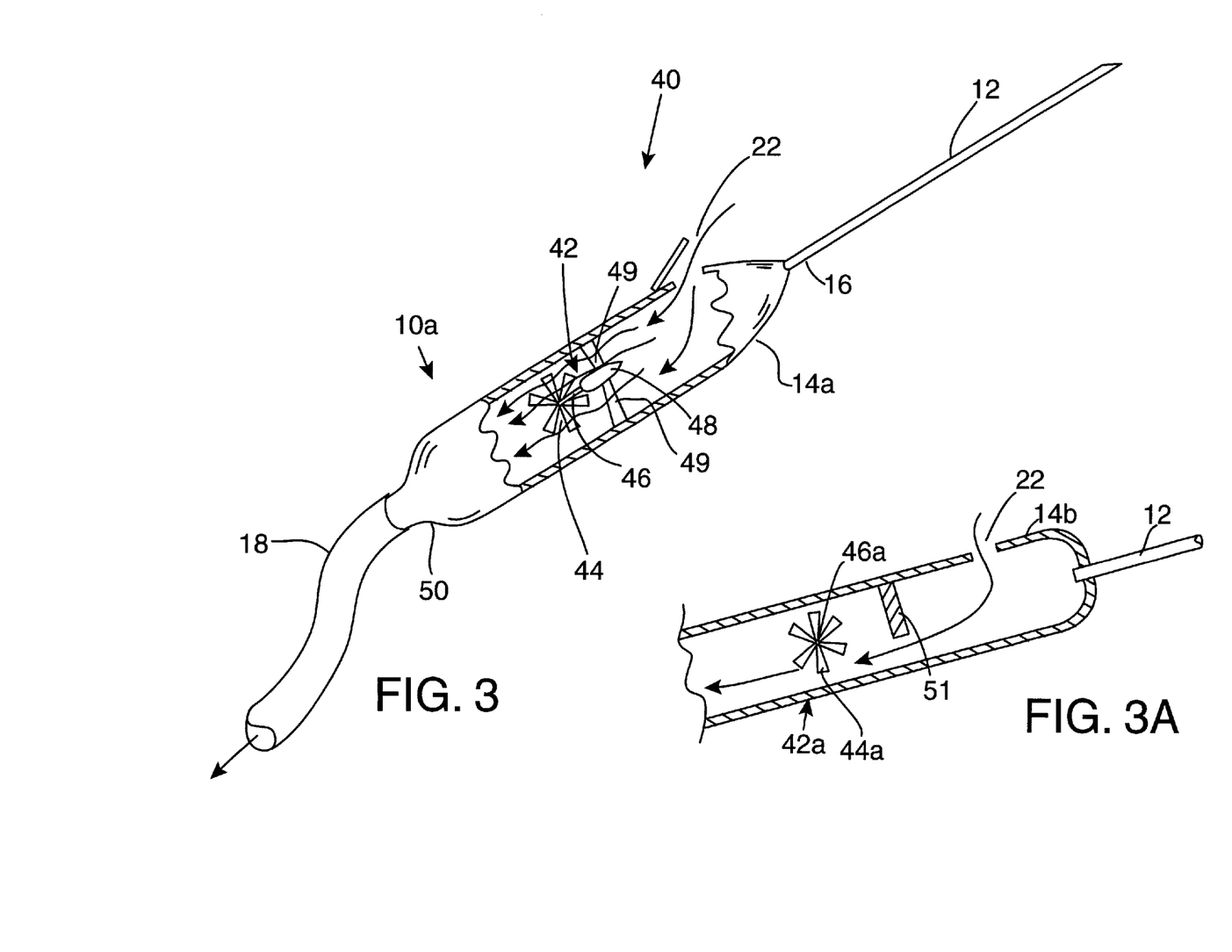
FIG. 3 is a partially cut away perspective view of a vibrating needle apparatus of the invention, the cut away in the handle revealing a vibration generator.
FIG. 3A is a cut away view showing an alternative vibration generator in the handle.

FIG. 3 shows a modified surgical needle apparatus 10a similar to the needle 10 of FIG. 1 but with a different vibrator. In FIG. 3 the apparatus 10a is shown with a needle 12 similar to the earlier embodiment, but with a handle or housing 14a which shows an example of a different type of vibrating device 42. The vibrator 42 comprises a vaned wheel or turbine-like device 44 mounted for rotation on a longitudinal shaft 46, secured via a bearing 48 and struts 49 to the housing 14a. The vaned wheel or turbine 44 is eccentrically weighted so that a wobble-type of vibration is induced and transmitted into the handle or housing 14a, in turn transferred to the needle 12. Air drawn through a suction line 18 connected at a back end 50 of the housing is drawn at the appropriate velocity, via a vent door 22, to produce vibration at the desired frequency. The vent door 22 can be selectively opened for use of the vibrating feature, or closed for inducing suction through the hollow needle 12.

Other forms of air-operated vibration inducing mechanisms can be used. For example, a paddle wheel-type vibrator 42a as shown in FIG. 3A can be mounted in the housing with an axis 46a transverse to the length of the housing, and with only one edge of the paddle wheel exposed to the rushing air, via a partial partition 51 so that air passes tangentially over the paddle wheel blades. Again, such a wheel 42a has eccentric weighting, as by a weighted blade or vane 44a, so as to cause the desired vibration in the handle and hence in the needle 12.

Figure 4:
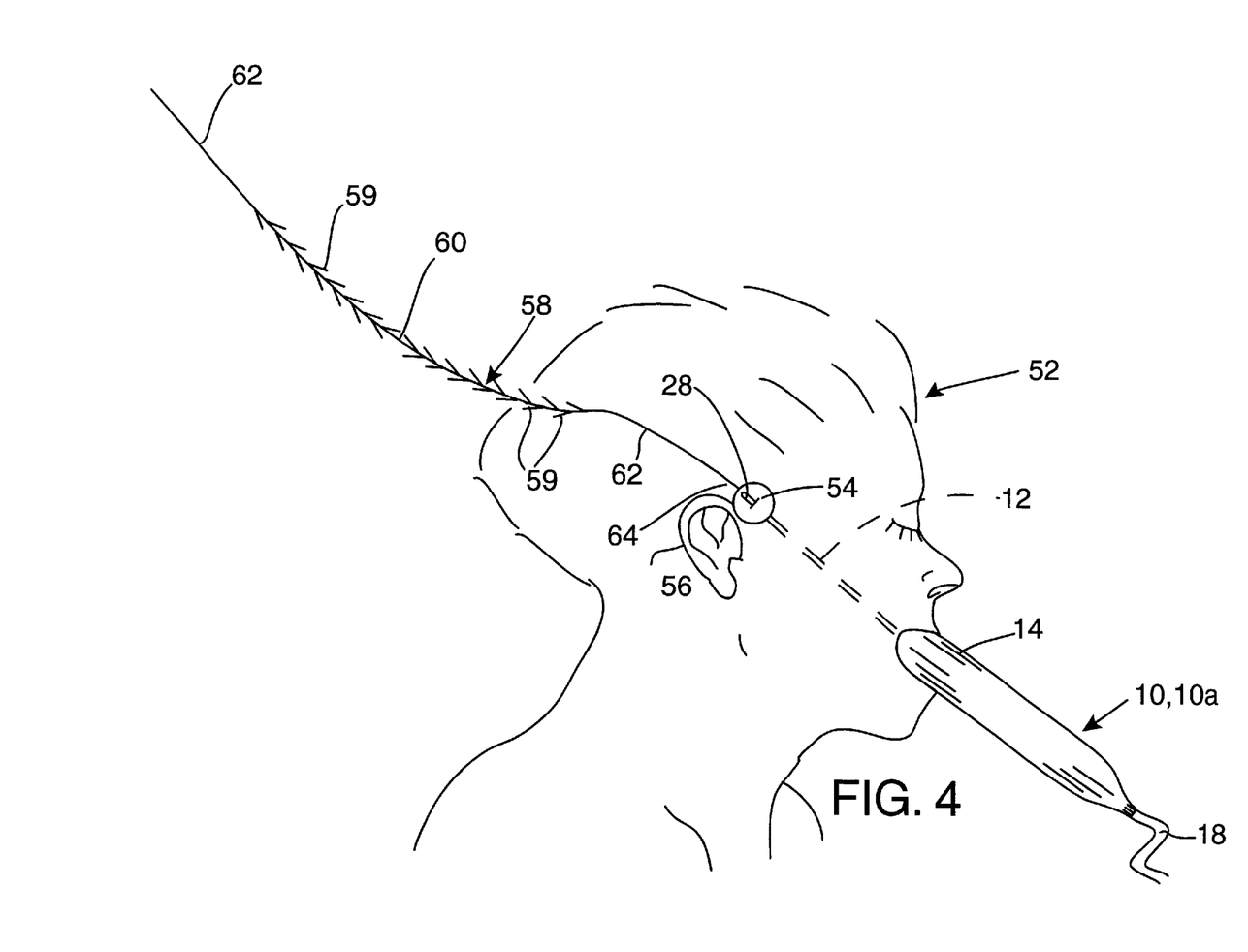
FIG. 4 is a view showing a profile of a patient and demonstrating schematically one step in a face-lift operation using a surgical needle according to principles of the invention, in conjunction with a one-way suture which is illustrated schematically.

FIG. 4 shows a step in use of the vibrating suction needle device 10 (or 10a) of the invention. In FIG. 4 the surgeon has inserted the needle 12 under the surface of the skin in a face-lift patient 52. The needle 12 is shown inserted virtually through its whole length, up to the distal end of the handle 14. The relatively long needle 12 has been caused to emerge at a small incision 54 which has been made for this purpose, and the distal end or tip 28 of the vibrating suction needle now extends out of the skin by the ear 56, as shown. The drawing shows a barbed suture 58, having barbs 59 extending in two directions: at the first or proximal side of a suture midpoint 60, the barbs 59 extend back as shown, so that the suture in this region can be pulled through tissue in a direction to the right as seen in FIG. 4, while a distal section of the suture 58, at a distal side of the midpoint 60, has barbs 59 which extend in the opposite direction, permitting passage through tissue only to the left as would be viewed in FIG. 4. The term "midpoint" is not intended to mean necessarily the center of the suture's length, but simply the location at which the barbs 59 change direction.

In a preferred form of the invention, the suture 58 has a smooth proximal end 62. Preferably there is also a smooth section 62 at the opposite end of the suture, at the opposite side of the midpoint 60. The smooth section 62 is designed to be drawn into the hollow needle 12, with suction applied through the needle via the suction tube 18 and the handle 14. As discussed above, when the suction is applied and the suture is inserted, the suture material is closely drawn into the hollow shank of the needle 12 and is firmly retained therein, to the extent that the handle 14 and needle 12 can be pulled back to draw the one-way suture, with the barbs 59, through the tissue up to the extent of the suture's midpoint 60.

The smooth section 62 on the suture is preferred, especially to allow the diameter of the needle to be as small as possible. An alternative less preferable is to have the suture with barbs 59 extending to its proximal end 64, without a smooth section. The suction applied through the needle 12 can still be sufficient to retain the suture within the needle for drawing through the tissue, although the inside diameter of the needle may have to be slightly larger.

If desired for further gripping of the suture, the handle or housing 14 can have an appropriate form of engaging clip (not shown) inside the housing, near its forward end, to grab the end of the suture when the suture is to be pulled through the patient's tissue. Such a clip can then be released by an external lever or button (not shown) after this operation is complete. The preferred gripping method is strictly by suction through the hollow needle.

As described above, the vibrating suction needle device 10 (or 10a) of the invention induces a vibration in the needle 12 via a vibrating device in the handle 14. This facilitates the insertion of the needle 12 through subcutaneous tissue substantially without damage to blood vessels, nerves, etc., so that when the needle has been fully inserted to the position shown in FIG. 4, internal damage to the patient's tissue is minimal. Needles of similar length are used routinely to infiltrate tissues for operations under local anaesthesia ("field blocks").

Figure 5:
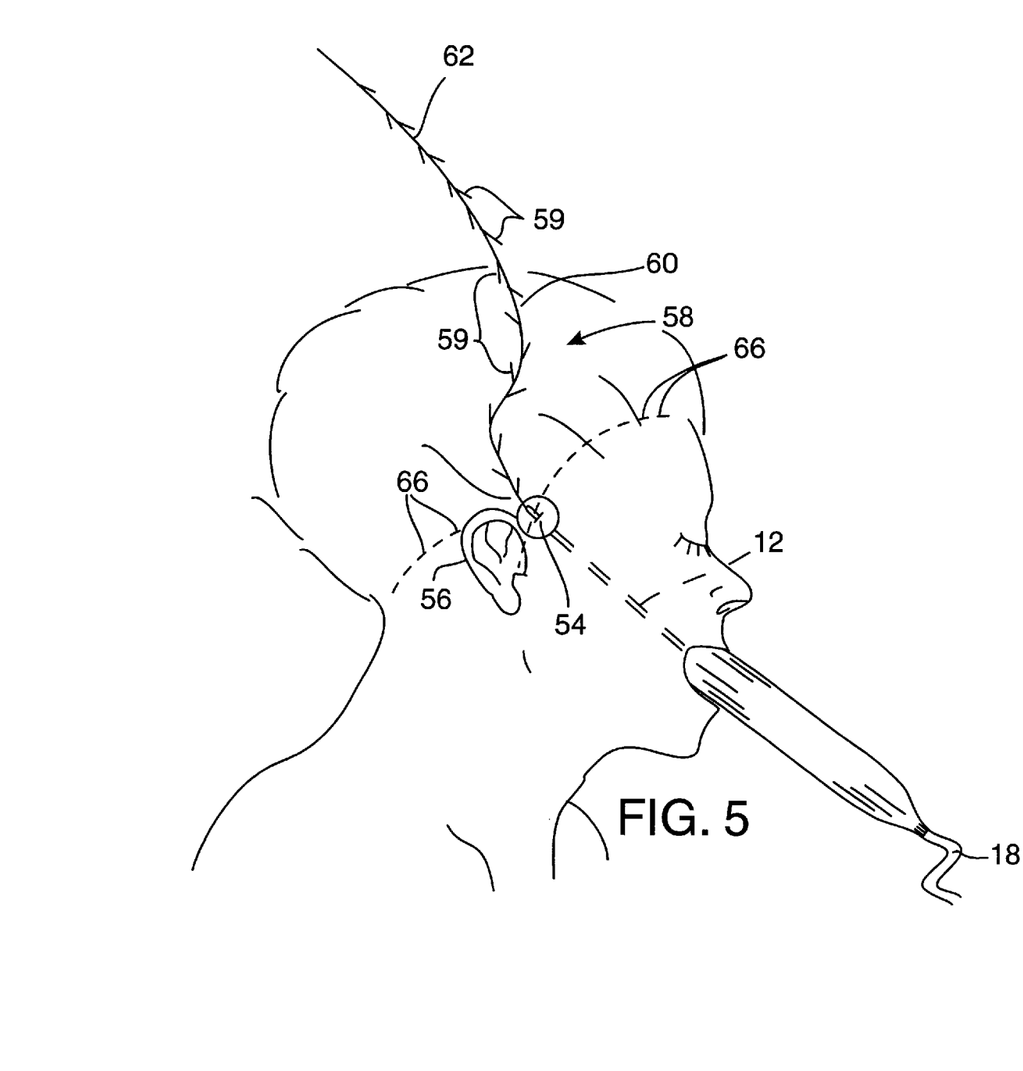
FIG. 5 is a view similar to FIG. 4, showing a further step in the same procedure.

FIG. 5 shows the procedure of FIG. 4 as carried to a further step. The proximal end of the suture 58 has been inserted into the open end of the needle 12 and drawn into the length of the needle via suction. This effects the gripping of the suture to the point that it can now be pulled through the tissue, to be placed along the same path which is shown as occupied by the needle 12 in FIG. 5.

FIG. 5 also shows a series of small incisions 66 which may be made on either side of the patient's ear 56, as proposed additional sites for placement of the one-way sutures 58. Each of these can be made just prior to needle insertion. The small incisions are made at the exit site of the needle tip to permit the suture to drop into a subcutaneous plane when both ends have been placed.

Figure 6:
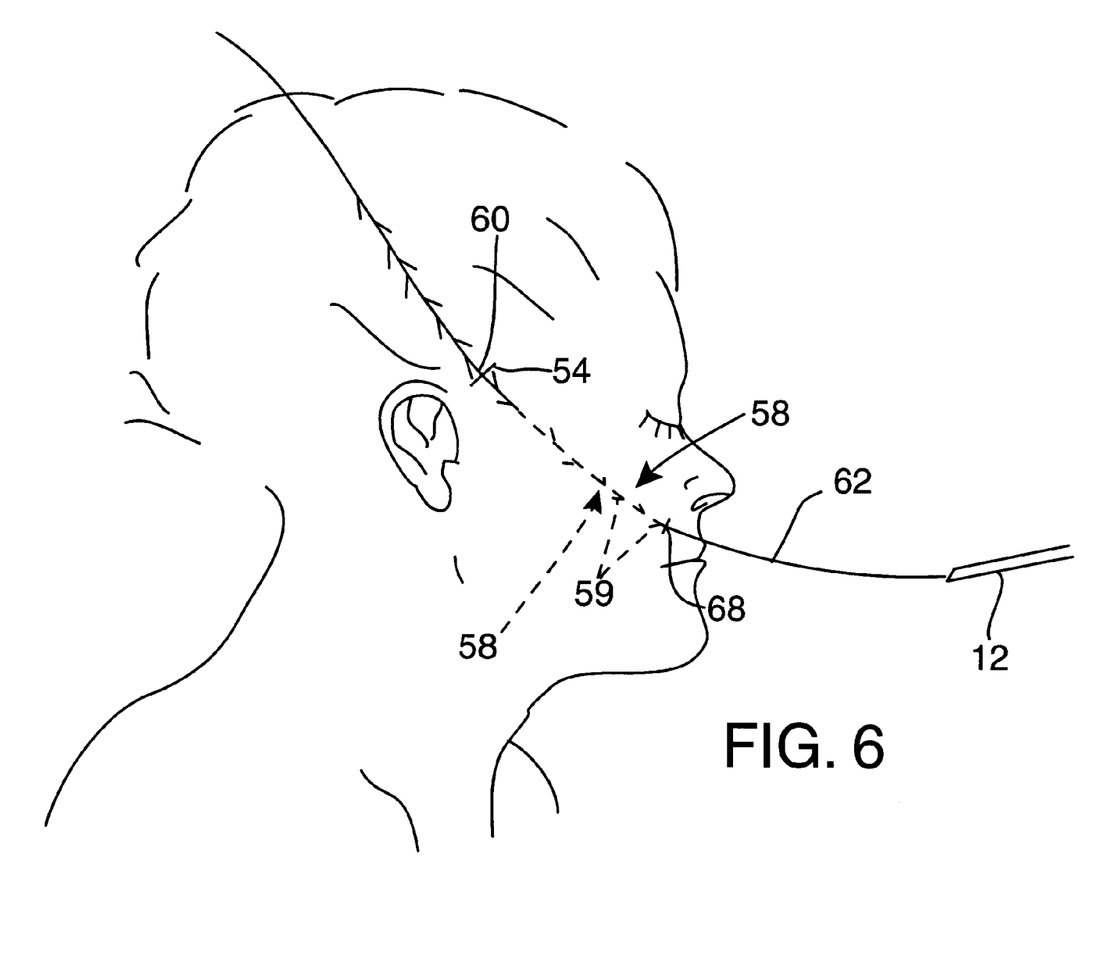
FIG. 6 is another similar view, showing a subsequent step wherein the one-way suture is pulled into place in subcutaneous tissue.

FIG. 6 shows the procedure at a further stage, at which the needle 12 has been retracted back out of the patient's tissue and is being released from the suture 58. FIG. 6 reveals that a proximal end length 62 of the suture has been pulled out from the skin, this length essentially being the length of the needle, since this proximal portion of the suture was engaged by suction within the needle as the needle was retracted. In a preferred embodiment, this proximal portion 62 is smooth and non-barbed, as discussed above.

At this point the suture has been pulled through the tissue to the extent that the barbs 59 lie under the skin and reach to or essentially to the puncture wound 68 where the needle was first inserted. The suture 58 is selected and appropriately proportioned such that the midpoint 60 of the suture, at which the barbs reverse direction, resides at the small incision 54 and under the skin surface. The surgeon is now ready to undertake placement of the distal end of the barbed suture 58 into the tissue.

Figure 7:
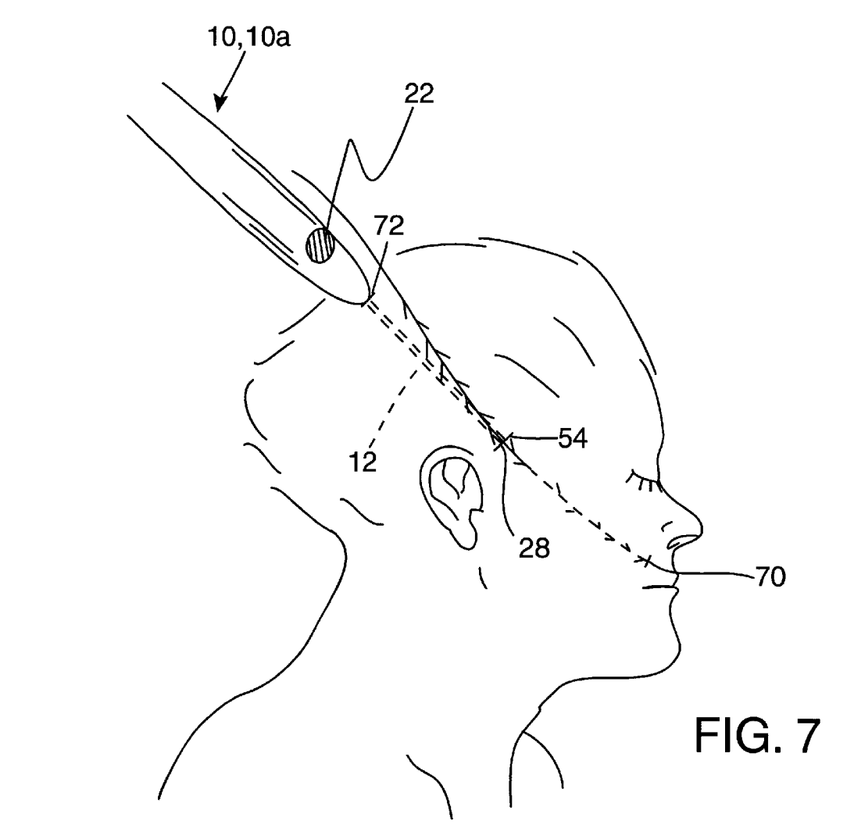
FIG. 7 is another similar view, showing another step in the face-lift procedure wherein the needle is again inserted under the skin.

In FIG. 7 the original proximal end portion 62 of the suture has been severed by the surgeon, leaving an end 70 beneath the patient's skin. The surgeon may elect to leave this end of the suture long until the end of the procedure, should final adjustments be needed. The surgeon has now inserted the needle 12, using vibrating mode, through the patient's tissue as shown, through a puncture wound point 72 to the point that the needle tip 28 has emerged from the tissue at the small midpoint incision 54. Once the vibrating needle has been so placed, vibration is turned off, by closing the vent 22 in this preferred form of the device, and suction is applied so as to draw air through the needle 12.

Figure 8:
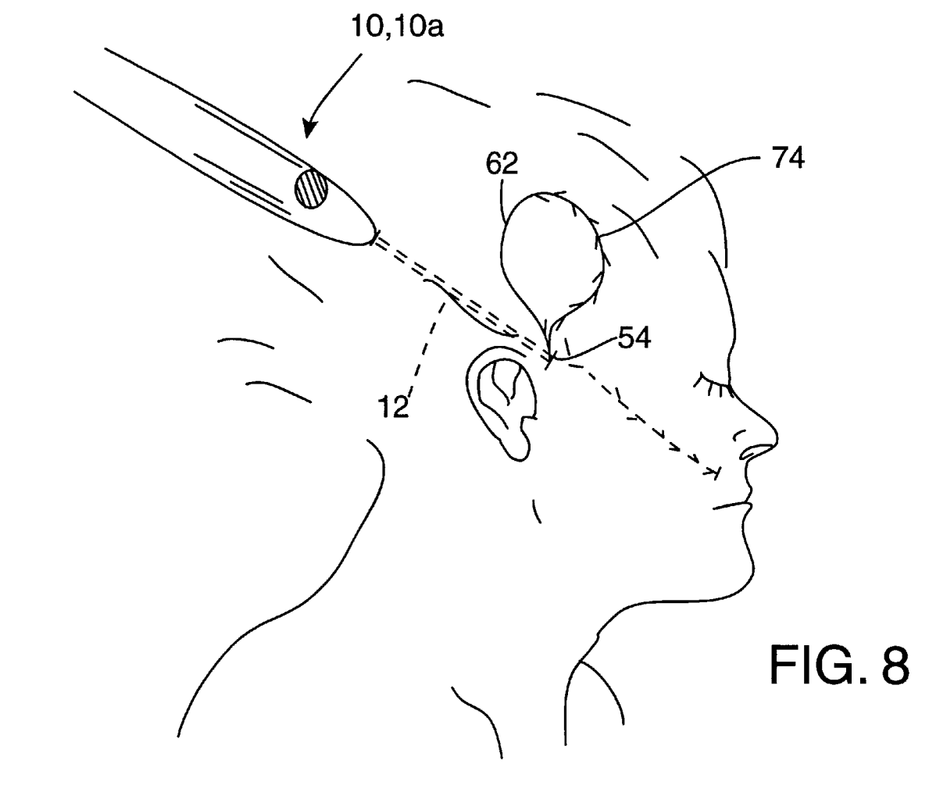
FIG. 8 is a similar view showing another step in the procedure.

FIG. 8 shows the procedure of feeding the original distal end portion 62 of the suture into the end of the hollow needle 12, at the midpoint incision 54. Again, this end portion 62 preferably is smooth and without barbs. The vibrating suction needle device 10 (or 10a) is set to the mode in which suction draws air through the needle by closing the vent 22, so that the device readily pulls the portion 62 of the suture into the shank of the needle and retains it there.

Once the suture end portion 62 has been fully drawn into the needle 12, the surgeon is ready to again retract the needle 12 from the patient's tissue. At this point (which is not shown in FIG. 9) the smooth portion 62 of the suture is fully ensconced in the needle, but the barbed portion 74 of the once-distal portion of the suture is slack and extends outside the patient's tissue, in a loop.

The surgeon retracts the needle 12, thus pulling the barbed portion 74 of the suture into the tissue, to reside in the path occupied by the needle in its position shown in FIG. 8. Following this, the needle is removed from the suture, by turning off suction to the needle to allow its easy retraction.

Figure 9:
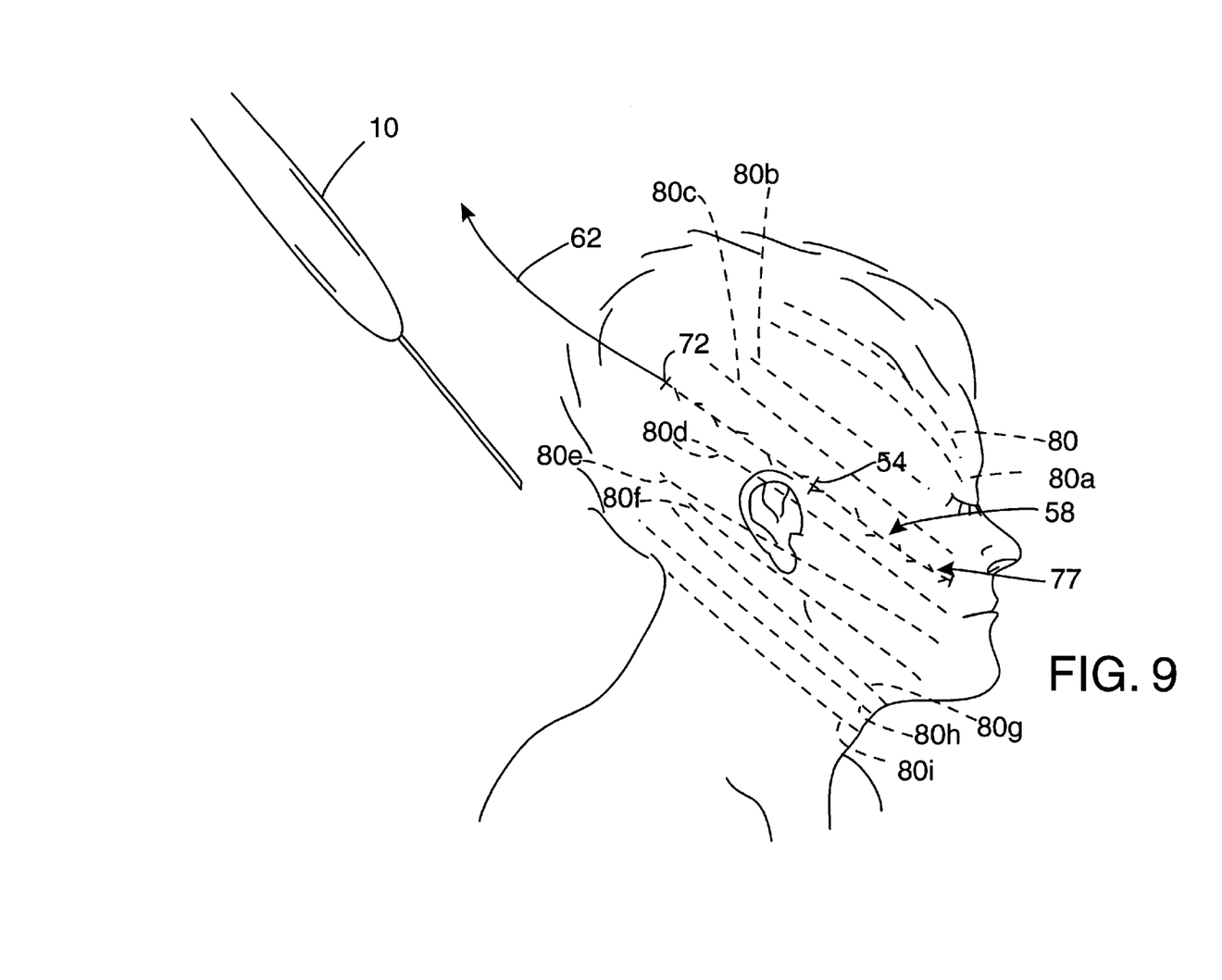
FIG. 9 is another similar view showing the patient in profile and indicating multiple paths where double-armed one-way sutures have been inserted using the methods and surgical appliance of the invention.

FIG. 9 shows the suture 58 as fully installed along a first desired line of support 77 in the face-lift operation, and with the needle apparatus 10 removed. The once-distal end 62 of the suture extends out the back of the line 77, from the rear puncture wound 72 as shown. At this point traction is applied by the surgeon to tension the one-way suture 58, thus supporting the tissue at the lower portion of the line of support 77 via the back or upper end of the suture with its reversed barbs, leading from the midpoint 54 back to the rear puncture wound 72. However, this traction can be applied later, after insertion of the desired number of additional one-way sutures as indicated in dashed lines at 80, 80a, 80b, 80c, 80d, 80e, 80f, 80g, 80h and 80i. The implanted tensioned sutures are left in place.

The above described preferred embodiments are intended to illustrate the principles of the invention, but not to limit its scope. Other embodiments and variations to this preferred embodiment will be apparent to those skilled in the art and may be made without departing from the spirit and scope of the invention as defined in the following claims.

I claim:

1. A surgical needle apparatus for passing through a patient's tissue while avoiding or minimizing damage to major blood vessels and nerves, comprising:

a needle with a proximal end and with a sharp distal end, and a handle attached to the proximal end of the needle, the handle having means for inducing vibration in the needle, such vibration being of a frequency which will cause the needle's distal end to tend to work its way around major blood vessels and nerves without substantial damage as the distal end is pushed through the patient's tissue.

2. The apparatus of claim 1, wherein the needle includes, at one of its ends, means for engaging a suture end to enable pulling the suture through the tissue after the needle has been passed through the tissue.

3. The apparatus of claim 1, wherein the means for inducing vibration comprises air-responsive vibration means within the handle, and including a pneumatic line connected to the handle so as to cause passage of air through the handle and through the vibration means, thus causing the needle to vibrate.

4. The apparatus of claim 3, wherein the pneumatic line is a suction line.

5. The apparatus of claim 3, wherein the vibration means comprises a rotatable wheel, eccentrically weighted, with blades responsive to air passage so as to cause rotation of the wheel.

6. The apparatus of claim 3, wherein the vibration means comprises a vibrating flutter valve through which air is directed by the pneumatic line.

7. The application of claim 1, wherein said vibration caused by the means for inducing vibration is in a frequency range well below ultrasonic.

8. The apparatus of claim 1, wherein said vibration caused by the means for inducing vibration is in the frequency range of about 20 to 30 hertz.

9. The apparatus of claim 2, wherein the means for engaging a suture end comprises the needle being hollow and open at its distal end, and of a diameter enabling the end of a suture to be drawn into the needle from the distal end, and including a suction line secured to the handle and means for causing suction from the suction line to be applied to the proximal end of the hollow needle so as to draw in the suture end, thereby holding the suture end to the needle.

10. The apparatus of claim 9, wherein the distal end of the hollow needle is angled, and wherein only a distal portion of the angled end is sharp, helping reduce damage to blood vessels and nerves as the needle is inserted through tissue.

11. The apparatus of claim 9, wherein the means for inducing vibration comprises air-responsive vibration means within the handle, with said suction line communicating with the vibration means and include a selectively openable vent in the handle such that, when the vent is opened, suction from the suction line causes passage of air through the handle and through the vibration means, thus causing the needle to vibrate, and such that when the vent is closed, all suction is drawn through the hollow needle.

* * * * *